United States Patent
Tang et al.

(10) Patent No.: US 12,059,467 B2
(45) Date of Patent: Aug. 13, 2024

(54) LOW-TOXICITY AND HIGH-EFFICIENCY ORTHOESTER MIXTURE PHARMACEUTICAL ADJUVANT, PREPARATION METHOD THEREOF, AND TOPICAL SUSTAINED RELEASE DRUG DELIVERY FORMULATION INCLUDING SAME

(71) Applicant: ANHUI UNIVERSITY, Hefei (CN)

(72) Inventors: Rupei Tang, Hefei (CN); Guoqing Yan, Hefei (CN); Xin Wang, Hefei (CN)

(73) Assignee: ANHUI UNIVERSITY, Hefei (CN)

( * ) Notice: Subject to any disclaimer, the term of this patent is extended or adjusted under 35 U.S.C. 154(b) by 0 days.

(21) Appl. No.: 18/278,416

(22) PCT Filed: Aug. 24, 2022

(86) PCT No.: PCT/CN2022/114445
§ 371 (c)(1),
(2) Date: Aug. 23, 2023

(87) PCT Pub. No.: WO2023/221320
PCT Pub. Date: Nov. 23, 2023

(65) Prior Publication Data
US 2024/0108728 A1    Apr. 4, 2024

(30) Foreign Application Priority Data
May 20, 2022 (CN) .......................... 202210550554.3

(51) Int. Cl.
*A61K 47/22* (2006.01)
*A61K 31/337* (2006.01)
(Continued)

(52) U.S. Cl.
CPC ............ *A61K 47/22* (2013.01); *A61K 31/337* (2013.01); *A61K 31/415* (2013.01);
(Continued)

(58) Field of Classification Search
CPC ............................... A61K 31/337; A61K 47/22
See application file for complete search history.

(56) References Cited

U.S. PATENT DOCUMENTS

| | | |
|---|---|---|
| 6,166,137 A | 12/2000 | Brown et al. |
| 2009/0011133 A1 | 1/2009 | Gridnev et al. |
| 2013/0209566 A1 | 8/2013 | Jablonski et al. |

FOREIGN PATENT DOCUMENTS

| | | |
|---|---|---|
| CN | 103804339 A | 5/2014 |
| CN | 103804684 A | 5/2014 |

(Continued)

OTHER PUBLICATIONS

Wang Zhuyong, et al., Application Progress of Prodrug for the Research of the Targeted Antitumor Drugs, Chin J Mod Appl Pharm, 2021, pp. 2323-2332, vol. 38, No. 18.
(Continued)

*Primary Examiner* — Carlos A Azpuru
(74) *Attorney, Agent, or Firm* — Bayramoglu Law Offices LLC

(57) ABSTRACT

An improved low-toxicity and high-efficiency orthoester mixture pharmaceutical adjuvant, a preparation method thereof, and a topical sustained release drug delivery formulation including the same are provided. The improved low-toxicity and high-efficiency orthoester mixture pharmaceutical adjuvant is obtained by mixing methoxy-free orthoester compounds (classes I and II) in different proportions or mixing an orthoester compound (class I or II) with a biocompatible medical polymer material in different proportions, where an orthoester compound of class I has a chemical formula shown in formula I:

(Continued)

and an orthoester compound of class II has a chemical formula shown in formula II:

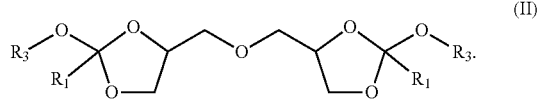

(II)

The present disclosure has the following beneficial effects: In the present disclosure, the biosafety of the pharmaceutical adjuvant is improved by adjusting a substituent type and a length of an orthoester compound, and the properties of the orthoester mixture pharmaceutical adjuvant do not change before and after the improvement.

20 Claims, 11 Drawing Sheets

(51) Int. Cl.
| | | |
|---|---|---|
| *A61K 31/415* | (2006.01) | |
| *A61K 31/4184* | (2006.01) | |
| *A61K 31/445* | (2006.01) | |
| *A61K 38/28* | (2006.01) | |
| *A61K 38/38* | (2006.01) | |
| *A61K 47/34* | (2017.01) | |
| *C07D 317/34* | (2006.01) | |

(52) U.S. Cl.
CPC ........ *A61K 31/4184* (2013.01); *A61K 31/445* (2013.01); *A61K 38/28* (2013.01); *A61K 38/38* (2013.01); *A61K 47/34* (2013.01); *C07D 317/34* (2013.01)

(56) References Cited

FOREIGN PATENT DOCUMENTS

| | | | |
|---|---|---|---|
| CN | 111073002 A | | 4/2020 |
| CN | 114366711 | * | 4/2022 |
| CN | 114366711 A | | 4/2022 |
| CN | 114848585 | * | 8/2022 |
| CN | 114848585 A | | 8/2022 |

OTHER PUBLICATIONS

Tell Tuttle, et al., Hemiortho Esters and Hydrotrioxides as the Primary Products in the Low-Temperature Ozonation of Cyclic Acetals: An Experimental and Theoretical Investigation, J. Am. Chem. Soc., 2004, pp. 16093-16104, vol. 126, No. 49.

* cited by examiner

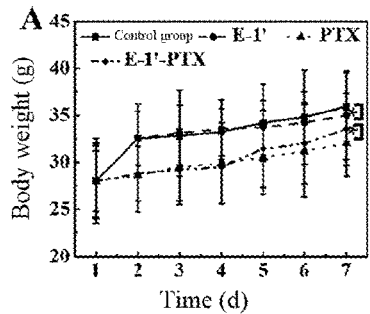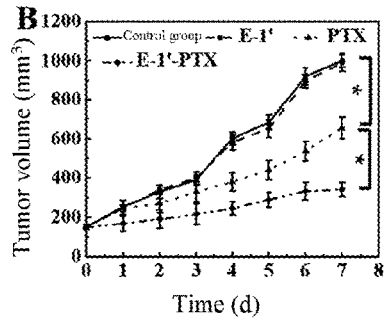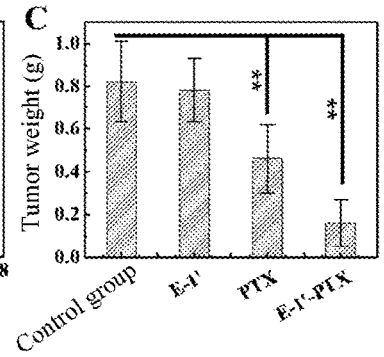
FIG. 5A FIG. 5B FIG. 5C
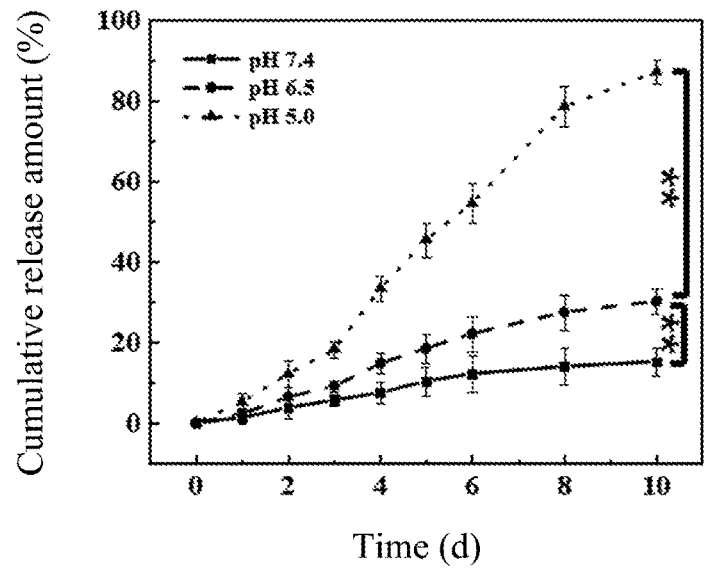
FIG. 6
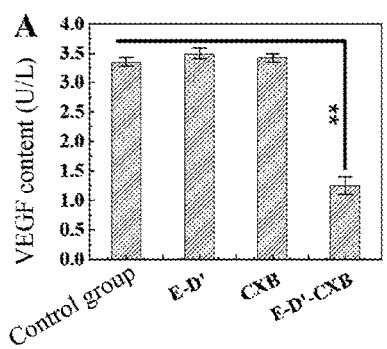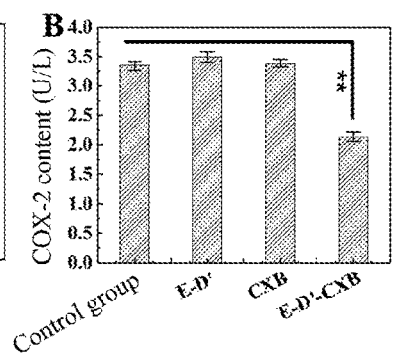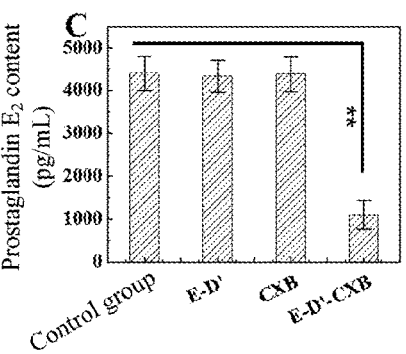
FIG. 7A FIG. 7B FIG. 7C

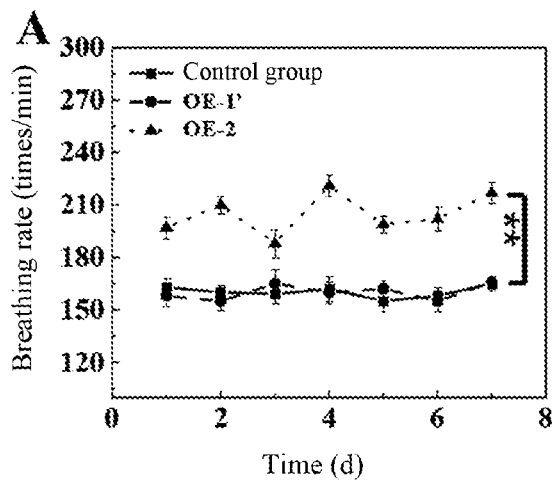
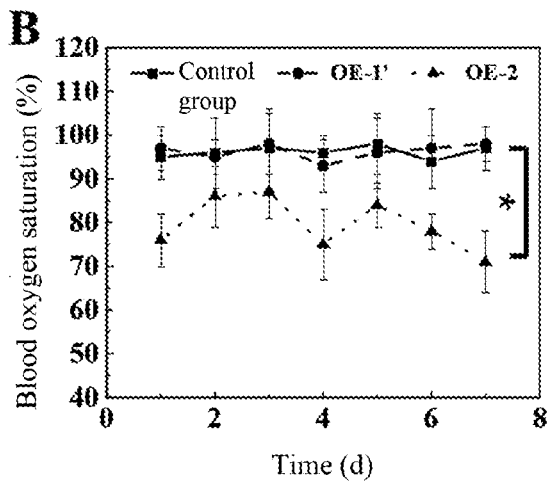
FIG. 18A   FIG. 18B
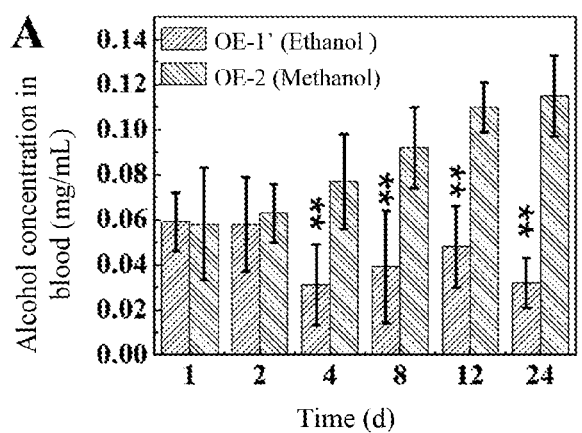
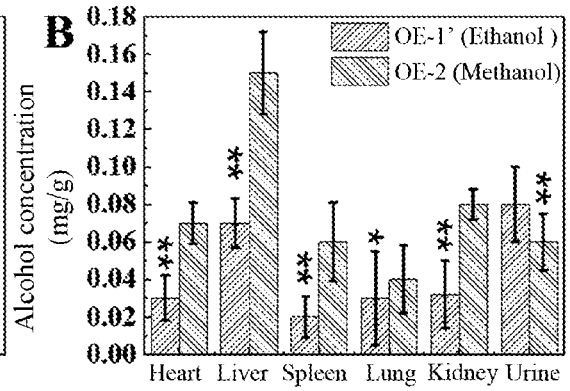
FIG. 19A   FIG. 19B

LOW-TOXICITY AND HIGH-EFFICIENCY ORTHOESTER MIXTURE PHARMACEUTICAL ADJUVANT, PREPARATION METHOD THEREOF, AND TOPICAL SUSTAINED RELEASE DRUG DELIVERY FORMULATION INCLUDING SAME

CROSS REFERENCE TO THE RELATED APPLICATIONS

This application is the national phase entry of International Application No. PCT/CN2022/114445, filed on Aug. 24, 2022, which is based upon and claims priority to Chinese Patent Application No. 202210550554.3, filed on May 20, 2022, the entire contents of which are incorporated herein by reference.

TECHNICAL FIELD

The present disclosure relates to the field of pharmaceutical adjuvants, and in particular relates to an improved low-toxicity and high-efficiency orthoester mixture pharmaceutical adjuvant, a preparation method thereof, and a topical sustained release drug delivery formulation including the same.

BACKGROUND

Pharmaceutical adjuvants refer to additives and excipients added in the production of a drug and formulation of a prescription, and when used in a pharmaceutical formulation, a pharmaceutical adjuvant is mainly intended to improve the availability of the pharmaceutical formulation or reduce the side effects. Pharmaceutical adjuvants can also be interpreted as a general term for substances whose safety is guaranteed other than active ingredients. Therefore, the biosafety of a pharmaceutical adjuvant is a prerequisite for clinical practice of the pharmaceutical adjuvant.

Orthoesters are a class of acid-sensitive degradable materials, which is widely studied and used in clinical practice as systemic or topical pharmaceutical adjuvants. The efficacy and safety of an orthoester pharmaceutical adjuvant depend on the structures of the orthoester pharmaceutical adjuvant and degradation products thereof.

Chinese patent application CN114366711A discloses an orthoester mixture pharmaceutical adjuvant, a preparation method thereof, and a topical sustained release drug delivery formulation including the same, where the orthoester mixture pharmaceutical adjuvant is mainly obtained by mixing different orthoester compounds in different proportions or mixing an orthoester compound with a biocompatible medical polymer material in different proportions. However, the orthoester compound used in the orthoester mixture pharmaceutical adjuvant includes methoxy, and a degradation product of the orthoester compound is methanol, which has the following potential biosafety risks: due to strong toxicity, methanol may largely impact the nervous system and the blood system of a human body and may lead to a toxic response after being taken in through the digestive tract, respiratory tract, or skin, and a vapor of methanol may damage the respiratory mucosa and vision of a human body, thereby causing harm to the human body; common symptoms of methanol poisoning include headache, nausea, vomiting, and blurred vision, and in severe cases, methanol poisoning may cause blindness and even death or may cause permanent damage to cranial nerves; and after entering the blood, methanol will damage kidneys and may even cause kidney failure in severe cases. Therefore, the orthoester compound used in the orthoester mixture pharmaceutical adjuvant needs to be improved to enhance the safety of the orthoester mixture pharmaceutical adjuvant.

SUMMARY

The technical problem to be solved by the present disclosure is to reduce the medication hazard of the existing orthoester mixture pharmaceutical adjuvant, eliminate the metabolic toxicity of the existing orthoester mixture pharmaceutical adjuvant, and improve the medication safety of the existing orthoester mixture pharmaceutical adjuvant, and provide an improved low-toxicity and high-efficiency orthoester mixture pharmaceutical adjuvant, a preparation method thereof, and a topical sustained release drug delivery formulation including the same accordingly.

The present disclosure solves the above technical problem through the following technical solutions:

The present disclosure provides an improved low-toxicity and high-efficiency orthoester mixture pharmaceutical adjuvant obtained mainly by mixing methoxy-free orthoester compounds (classes I and II) in different proportions or mixing an orthoester compound (class I or II) with a biocompatible medical polymer material in different proportions, where an orthoester compound of class I has a chemical formula shown in formula I:

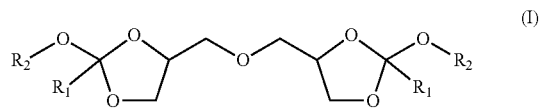

where $R_1$ is selected from the group consisting of hydrogen, methyl, ethyl, propyl, isopropyl, butyl, and phenyl, and $R_2$ is selected from the group consisting of ethyl, propyl, isopropyl, butyl, isobutyl, and tert-butyl; and an orthoester compound of class II has a chemical formula shown in formula II:

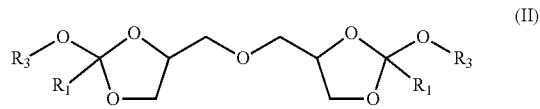

where $R_1$ is selected from the group consisting of hydrogen, methyl, ethyl, propyl, isopropyl, butyl, and phenyl, and $R_3$ is selected from the group consisting of a monomethyl ether polyethylene glycol (PEG) group, a monomethyl ether polypropylene glycol (PPG) group, a polyethylene (PE) group, an ester-terminated polylactic acid (PLA) group, an ester-terminated polycaprolactone (PCL) group, a polyether lauryl alcohol group, and a polyoxyethylene ether fatty alcohol group.

Beneficial effects: In the present disclosure, the biosafety of the pharmaceutical adjuvant is improved by adjusting a substituent type and a length of an orthoester compound, and the properties of the orthoester mixture pharmaceutical adjuvant do not change before and after the improvement, where the properties include, but are not limited to, all functions and effects of the orthoester mixture pharmaceutical adjuvant before structural improvement.

The improved orthoester mixture pharmaceutical adjuvant has an excellent dissolving capacity and can dissolve small molecules and protein drugs, exhibits prominent biocompatibility, can be clearly metabolized, and can be easily transformed and used in clinical practice. The improved orthoester mixture pharmaceutical adjuvant can be used to prepare a topical injection, a cream, or an ointment, and after the topical injection, cream, or ointment is locally injected or smeared, an active substance can be slowly and evenly released to play a long-lasting treatment role, which significantly improves the treatment index and compliance of a patient and has a wide range of clinical application values.

Preferably, a ratio of the orthoester compound of class I to the orthoester compound of class II is 1:1,000 to 1,000:1, and a ratio of the orthoester compound (class I or II) to the biocompatible medical polymer material is 1:1,000 to 1,000:1.

Beneficial effect: The fluidity, solubility, and degradation rate of the mixture is adjusted through the above ratio.

Preferably, the biocompatible medical polymer material is selected from the group consisting of:

(i) PCL

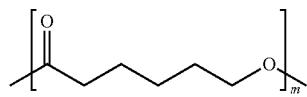
(II)

where m represents an integer of 2 to 100;

(ii) polycaprolactone diol (PCL-diol)

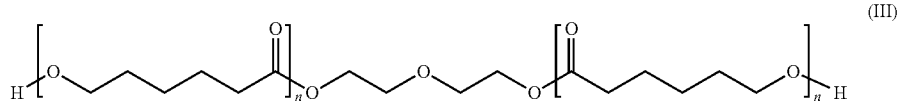
(III)

where n represents an integer of 1 to 50;

(iii) PLA

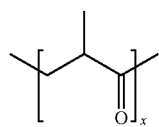
(IV)

where x represents an integer of 2 to 100; and (iv) PEG

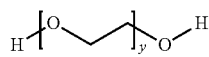
(V)

where y represents an integer of 2 to 150.

Preferably, a preparation method of the orthoester compound of class I includes the following steps: under protection of nitrogen, dissolving diglycerol, a triester, and a catalyst in a molar ratio of 1:(2.2-5.0):(0.01-0.04) in a first organic solvent, and stirring a resulting solution at room temperature to allow a reaction for 12 h to 48 h; and conducting extraction with saturated sodium carbonate, drying a resulting extract solution with anhydrous magnesium sulfate, and conducting vacuum distillation to remove the excess triester to obtain the orthoester compound of class I.

Preferably, a preparation method of the orthoester compound of class II includes the following steps: adding the orthoester compound of class I, a monoalcohol, and a catalyst in a molar ratio of 1:(2.2-8.0):(0.01-0.04) to a reaction vessel, stirring a resulting mixture at 135° C. under reduced pressure to allow a reaction for 2 h to 8 h, and conducting dialysis with the first organic solvent to remove the excess monoalcohol to obtain the orthoester compound of class II.

Beneficial effect: The preparation method of the orthoester compound in the present disclosure is simple and involves one-step preparation at room temperature and constant pressure; and a structure of an orthoester compound prepared by the preparation method only includes carbon-oxygen bonds, which will not destroy a structure of a drug.

Preferably, the first organic solvent is selected from the group consisting of acetonitrile, dichloromethane (DCM), tetrahydrofuran (THF), and dioxane; the triester is selected from the group consisting of triethyl orthoformate, triethyl orthoacetate, triethyl orthopropionate, triethyl orthoisopropionate, triethyl orthobutyrate, triethyl orthobenzoate, tripropyl orthoformate, tripropyl orthoacetate, tripropyl orthopropionate, tripropyl orthoisopropionate, tripropyl orthobutyrate, tripropyl orthobenzoate, triisopropyl orthoformate, triisopropyl orthoacetate, triisopropyl orthopropionate, triisopropyl orthoisopropionate, triisopropyl orthobutyrate, triisopropyl orthobenzoate, tributyl orthoformate, tributyl orthoacetate, tributyl orthopropionate, tributyl orthoisopropionate, tributyl orthobutyrate, tributyl orthobenzoate, triisobutyl orthoformate, triisobutyl orthoacetate, triisobutyl orthopropionate, triisobutyl orthoi sopropionate, trii sobutyl orthobutyrate, trii sobutyl orthobenzoate, tri-tert-butyl orthoformate, tri-tert-butyl orthoacetate, tri-tert-butyl orthopropionate, tri-tert-butyl orthoisopropionate, tri-tert-butyl orthobutyrate, and tri-tert-butyl orthobenzoate; the monoalcohol is selected from the group consisting of PEG monomethyl ether, PPG monomethyl ether, PE monoalcohol, ester-terminated PLA, ester-terminated PCL, laureth, and fatty alcohol polyoxyethylene ether; and the catalyst is selected from the group consisting of p-toluenesulfonic acid (PTSA) and pyridinium p-toluenesulfonate (PPTS).

The present disclosure also provides a preparation method of the improved low-toxicity and high-efficiency orthoester mixture pharmaceutical adjuvant, including the following step: mixing the orthoester compound of class I with the orthoester compound of class II or mixing an orthoester compound (class I or II) with a biocompatible medical polymer material, where the mixing is conducted at 25° C. to 140° C. under a negative pressure or at 25° C. to 140° C. in a nitrogen atmosphere; or the raw materials are first dissolved in a second organic solvent, and then the second organic solvent is removed under reduced pressure.

Beneficial effects: The pharmaceutical adjuvant in the present disclosure has metabolic products with low toxic and side effects in vivo and retains the following advantages: The pharmaceutical adjuvant can be prepared by a simple preparation method. The orthoester compound only includes carbon-oxygen bonds, which will not destroy a structure of a drug. Because the orthoester compound itself is a liquid, the orthoester compounds can be mixed with each other or the orthoester compound can be mixed with a solid, semi-solid, or liquid biocompatible medical polymer material according to needs to obtain an orthoester mixture pharmaceutical adjuvant with adjustable fluidity, solubility, degradation rate, and sustained release rate, and each batch can be completely repeated.

The orthoester mixture pharmaceutical adjuvant has an excellent dissolving capacity and can dissolve small molecules and protein drugs, exhibits prominent biocompatibility, can be clearly metabolized, and can be easily transformed and used in clinical practice. The improved orthoester mixture pharmaceutical adjuvant can be used to prepare a topical injection, a cream, or an ointment, and after the topical injection, cream, or ointment is locally injected or smeared, an active substance can be slowly and evenly released to play a long-lasting treatment role, which significantly improves the treatment index and compliance of a patient and has a wide range of clinical application values.

Preferably, the second organic solvent is selected from the group consisting of THF, DCM, dioxane, ethanol, methanol, chloroform, acetone, dimethyl sulfoxide (DMSO), and N,N-dimethylformamide (DMF).

The present disclosure also provides a topical sustained release drug delivery formulation including the improved low-toxicity and high-efficiency orthoester mixture pharmaceutical adjuvant described above and an active substance, where the solubility, fluidity, degradation rate, and release rate of the active substance in the improved low-toxicity and high-efficiency orthoester mixture pharmaceutical adjuvant are determined; and a weight percentage of the active substance is 0.1% to 50%, and a weight percentage of the improved low-toxicity and high-efficiency orthoester mixture pharmaceutical adjuvant is 50% to 99.9%.

Beneficial effects: The improved low-toxicity and high-efficiency orthoester mixture pharmaceutical adjuvant in the present disclosure has metabolic products with low toxic and side effects in vivo and retains the following advantages: The improved low-toxicity and high-efficiency orthoester mixture pharmaceutical adjuvant can be compounded with an active substance to produce a drug delivery formulation in a form of an injection, a cream, or an ointment, and after the injection, cream, or ointment is locally injected or smeared, an active substance can be slowly and evenly released to play a long-lasting treatment role, which significantly improves the treatment index and compliance of a patient and has a wide range of clinical application values.

The solubility, fluidity, degradation rate, and release rate of the active substance in the improved low-toxicity and high-efficiency orthoester mixture pharmaceutical adjuvant are adjusted by adjusting the weight percentages of the active substance and the improved low-toxicity and high-efficiency orthoester mixture pharmaceutical adjuvant.

Preferably, the active substance is one or more selected from the group consisting of an antitumor drug, an anti-inflammatory drug, a hypoglycemic drug, an antihypertensive drug, an analgesic drug, and a protein vaccine.

Preferably, the active substance is selected from the group consisting of a sedative-hypnotic drug, an antiepileptic drug, an antipsychotic drug, an antidepressant drug, an antianxiety drug, an antimanic drug, an analgesic drug, an anaesthetic drug, a non-steroidal anti-inflammatory drug (NSAID), cholinergic and anticholinergic drugs, an anti-ulcer drug, a prokinetic drug, an antiemetic drug, an antiallergic drug, a drug acting upon an adrenergic receptor, a hypoglycemic drug, an antihypertensive drug, a diuretic drug, a cardiac drug, an antiarrhythmic drug, an antianginal drug, a lipid-regulating agent, a steroidal hormone drug, an antibiotic, a synthetic antimicrobial agent, an antiviral drug, an antitumor drug, and a therapeutic polypeptide or protein; and the active substance is in a form of a topical smeared ointment, a cream, or an injectable fluid.

Preferably, the antitumor drug includes, but is not limited to, chemotherapeutic drugs paclitaxel, doxorubicin, gemcitabine, 5-fluorouracil, camptothecin, hydroxycamptothecin, cisplatin, and carboplatin and targeted therapeutic drugs PD-1, gefitinib, erlotinib, sorafenib, and dasatinib. The active substance can be administered through local sustained release.

Preferably, the anti-inflammatory drug includes, but is not limited to, aspirin, sodium diclofenac, ibuprofen, flurbiprofen, ketoprofen, naproxen, indobufen, indomethacin, piroxicam, meloxicam, imrecoxib, celecoxib, dexamethasone, hydrocortisone, prednisolone, methylprednisolone, triamcinolone acetonide, fluocinolone, fludrocortisone, and beclomethasone. The anti-inflammatory drug is added at a therapeutically-effective amount.

Preferably, the hypoglycemic drug includes, but is not limited to, a first-line hypoglycemic drug such as insulin and analogues thereof, a sulfonylurea secretagogue, metformin, a α-glucosidase inhibitor, a thiazolidinedione (TZD) derivative sensitizer, a phenylanisic acid derivative secretagogue, a GLP-1 receptor agonist, and a DPP-4 enzyme inhibitor. The hypoglycemic drug is added at a therapeutically-effective amount.

Preferably, the antihypertensive drug includes, but is not limited to, a common antihypertensive drug such as a thiazide, a potassium-sparing diuretic, an aldosterone antagonist, a loop diuretic, a central antihypertensive drug, a ganglion-blocking drug, a noradrenergic nerve ending-blocking drug, an adrenoceptor-blocking drug, an angiotensin-converting enzyme (ACE) inhibitor, an angiotensin II receptor-blocking drug, a renin inhibitor, a dihydropyridine, a dihydropyridine, and a vasodilator. The antihypertensive drug is added at a therapeutically-effective amount.

Preferably, the analgesic drug includes, but is not limited to, a series of clinical drugs such as a receptor agonist, a receptor partial agonist, an opioid receptor antagonist, and an antipyretic analgesic. The analgesic drug is added at a therapeutically-effective amount.

Preferably, the protein vaccine includes a natural protein and a chemically-inactivated toxoid. The protein vaccine is added at a therapeutically-effective amount.

The present disclosure has the following advantages: The biosafety of the pharmaceutical adjuvant is improved by adjusting a substituent type and a length of an orthoester compound, and the properties of the orthoester mixture pharmaceutical adjuvant do not change before and after the improvement, where the properties include, but are not limited to, all functions and effects of the orthoester mixture pharmaceutical adjuvant before structural improvement.

The improved low-toxicity and high-efficiency orthoester mixture pharmaceutical adjuvant has an excellent dissolving capacity and can dissolve small molecules and protein drugs, exhibits prominent biocompatibility, can be clearly metabolized, and can be easily transformed and used in clinical practice. The improved orthoester mixture pharmaceutical adjuvant can be used to prepare a topical injection, a cream, or an ointment, and after the topical injection, cream, or ointment is locally injected or smeared, an active substance can be slowly and evenly released to play a long-lasting treatment role, which significantly improves the treatment index and compliance of a patient and has a wide range of clinical application values.

The solubility, fluidity, degradation rate, and release rate of the active substance in the improved low-toxicity and high-efficiency orthoester mixture pharmaceutical adjuvant are adjusted by adjusting the weight percentages of the active substance and the improved low-toxicity and high-efficiency orthoester mixture pharmaceutical adjuvant.

BRIEF DESCRIPTION OF THE DRAWINGS

FIGS. 5A-5C show tumor suppression results of a paclitaxel injection subcutaneously injected into a tumor-bearing mouse in Example 7 of the present disclosure;

FIG. 6 shows drug release results of a celecoxib injection in PBS at pH 7.4, 6.5, and 5.0 in Example 8 of the present disclosure;

FIGS. 7A-7C show expression levels of vascular endothelial growth factor (VEGF), COX-2, and prostaglandin E2 on day 7 after subcutaneous injection of a celecoxib injection into a mouse in Example 8 of the present disclosure, where FIG. 7A corresponds to the VEGF, FIG. 7B corresponds to the COX-2, and FIG. 7C corresponds to the prostaglandin E2;

FIG. 15A shows a survival rate of mice undergoing intraperitoneal injection, FIG. 15B shows a survival rate of mice undergoing subcutaneous injection, FIG. 15C shows a survival rate of mice undergoing oral administration, and FIG. 15D shows the MTD of mice;

FIG. 17A shows a change of the blood pressure level in mice and FIG. 17B shows a change of the heart rate in mice;

FIGS. 18A-18B show changes of a breathing rate and a blood oxygen saturation in mice subcutaneously injected with OE-1' and OE-2 in Example 16 of the present disclosure, where FIG. 18A shows a change of the breathing rate in mice and FIG. 18B shows a change of the blood oxygen saturation in mice;

FIGS. 19A-19B show a distribution of alcohol metabolites in mice subcutaneously injected with OE-1' and OE-2 in Example 17 of the present disclosure, where FIG. 19A shows a change of an alcohol concentration in blood and FIG. 19B shows changes of alcohol concentrations in various tissues and urine;

DETAILED DESCRIPTION OF THE EMBODIMENTS

In order to make the objectives, technical solutions, and advantages of the examples of the present disclosure clear, the technical solutions in the examples of the present disclosure will be clearly and completely described below with reference to the examples of the present disclosure. Apparently, the described examples are some rather than all of the examples of the present disclosure. All other examples obtained by a person of ordinary skill in the art based on the examples of the present disclosure without creative efforts shall fall within the protection scope of the present disclosure.

The experimental materials, reagents, and the like used in the following examples are all commercially available, unless otherwise specified.

If specific techniques or conditions are not indicated in an example, a process shall be conducted in accordance with the techniques or conditions described in literatures in the art or in accordance with a product specification.

Example 1

Synthesis of an Orthoester Compound 4,4'-(Oxybis (Methylene))Bis(2-Ethoxy-1,3-Dioxolane) (OE-1')

Figure 1:
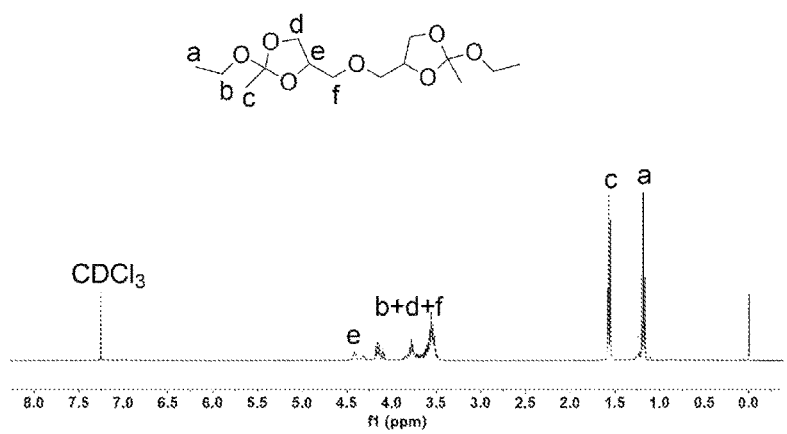
FIG. 1 is a proton nuclear magnetic resonance ($^1$H NMR) spectrum of the orthoester OE-1' in Example 1 of the present disclosure.
Figure 2A:
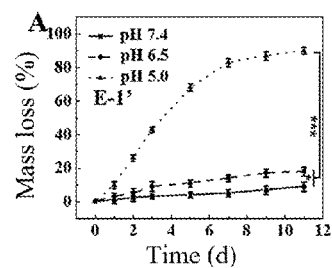
FIGS. 2A-2G show a change trend of a mass loss of each of E-1' to E-7' at different pH values in Example 5 of the present disclosure, where FIG. 2A to FIG. 2G correspond to E-1' to E-7', respectively.
Figure 2B:
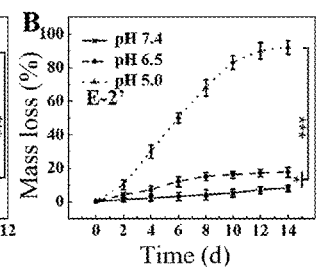
Figure 2C:
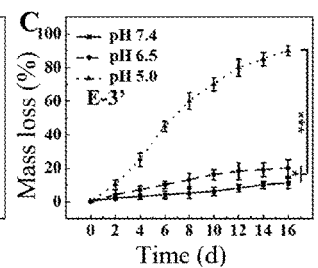
Figure 2D:
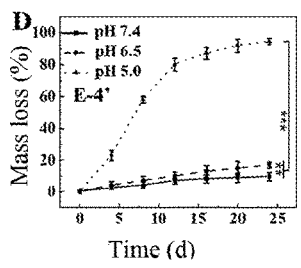
Figure 2E:
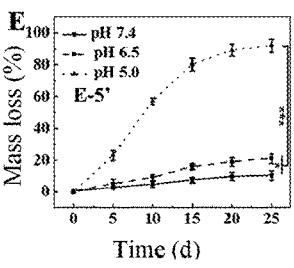
Figure 2F:
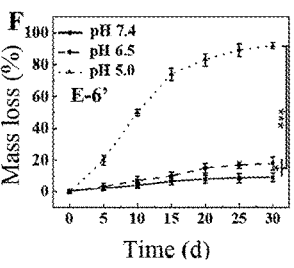
Figure 2G:
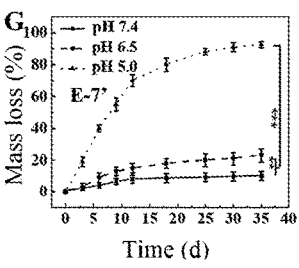
Figure 3A:
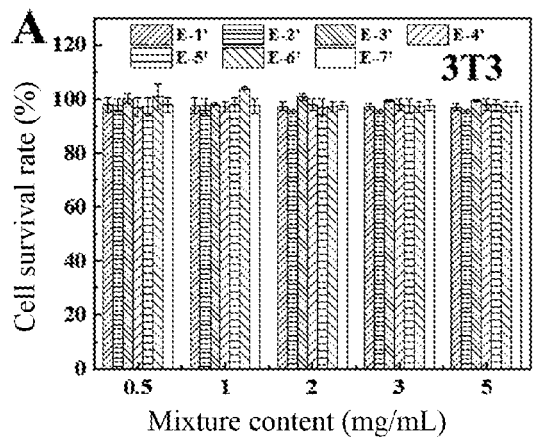
FIGS. 3A-3D show a change of cytotoxicity of each of E-1' to E-7' (FIG. 3A and FIG. 3B) and E-A' to E-D' (FIG. 3C and FIG. 3D) for 3T3 and QSG cells with a concentration in Example 6 of the present disclosure.
Figure 3B:
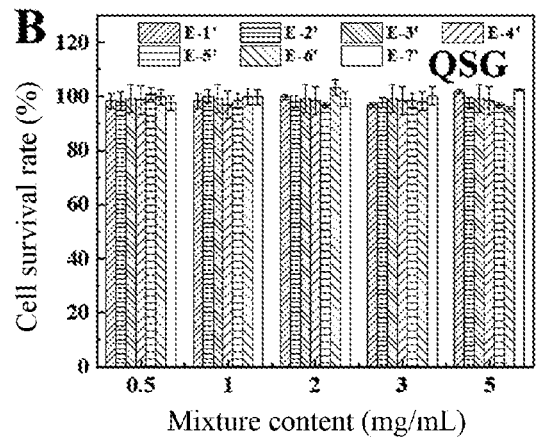
Figure 3C:
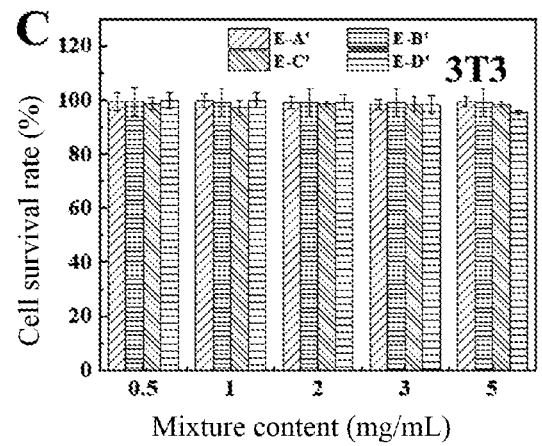
Figure 3D:
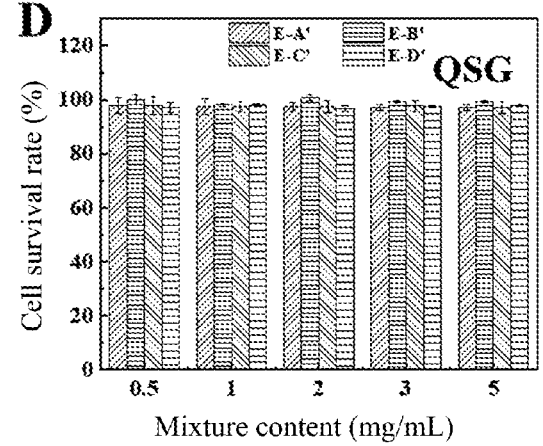

Under protection of nitrogen, diglycerol (16.6 g, 0.1 mol), triethyl orthoacetate (48.67 g, 0.3 mol), and PTSA (344.4 mg, 0.002 mol) were added to a reaction vessel, acetonitrile (150 mL) was added for dissolution, and a reaction was conducted overnight at room temperature; acetonitrile was removed from a crude product through vacuum distillation, and then ethyl acetate was added for dissolution; and extraction was conducted with a saturated sodium carbonate solution, and an extract solution was dried with anhydrous magnesium sulfate and then subjected to vacuum distillation to remove the ethyl acetate and the excess triethyl orthoacetate to obtain a colorless oily product, with a yield of 78.4%. $^1$H NMR of the product was shown in FIG. 1.

Example 2

Synthesis of an Orthoester Compound 4,4'-(Oxybis (Methylene))Bis(2-Propoxy-1,3-Dioxolane) (OE-2')

Under protection of nitrogen, diglycerol (16.6 g, 0.1 mol), tripropyl orthoacetate (61.25 g, 0.3 mol), and PTSA (344.4 mg, 0.002 mol) were added to a reaction vessel, acetonitrile (150 mL) was added for dissolution, and a reaction was conducted overnight at room temperature; acetonitrile was removed from a crude product through vacuum distillation, and then ethyl acetate was added for dissolution; and extraction was conducted with a saturated sodium carbonate solution, and an extract solution was dried with anhydrous magnesium sulfate and then subjected to vacuum distillation to remove the ethyl acetate and the excess triethyl orthoacetate to obtain a colorless oily product, with a yield of 76.2%.

Example 3

Synthesis of an Orthoester Compound 4,4'-(Oxybis (Methylene))Bis(2-(2-Methoxymonomethyl Ether PEGyl)-1,3-Dioxolane) (OE-3')

OE-1' (30.6 g, 0.1 mol), PEG 550 monomethyl ether (165.0 g, 0.3 mol), and PPTS (502.6 mg, 0.002 mol) were added to a reaction vessel, and a reaction was conducted at 135° C. under reduced pressure for 4 h; and a crude product was purified through dialysis with THF including a trace amount of triethylamine (TEA), where a dialysis bag used had a molecular weight cut-off (MWCO) of 1,000 daltons and a yield was 84.4%.

Example 4

Preparation of a Mixture of OE-1' with each of PCL-Diol (Mn=530), PCL (Mn=2,000), PEG (Mn=500), PLA (Mn=600), and OE-2'

At room temperature and in a nitrogen atmosphere, OE-1' and PCL-diol (Mn=530) were weighed according to mass ratios of 1:1, 1:3, 1:5, 1:7, 1:9, 1:11, and 1:13, added to beakers, and stirred for 30 min to obtain mixtures E-1' to E-7', respectively.

At 75° C. and under a negative pressure, OE-1' and each of PCL (Mn=2,000), PEG (Mn=500), PLA (Mn=3,000), and OE-2' were weighed according to mass ratios of 20:3, 30:1, 15:1, and 1:4, added to pear-shaped reaction vessels, and stirred for 30 min to obtain mixtures E-A', E-B', E-C', and E-D', respectively.

Example 5

Mass Loss Detection 0.5 g of each of the mixtures E-1' to E-7' was accurately weighed and added to a threaded bottle with a cap, 20 mL of PBS at pH 5.0, 6.5, and 7.4 was added, and the threaded bottle was allowed to stand at 37° C.; the threaded bottle was taken out at a preset time point, the excess PBS was removed from the threaded bottle, and the remaining mass was measured; and a mass loss was calculated. The above operation was repeated three times, and results were shown in FIGS. 2A-2G. On the one hand, the seven polymers have a similar mass loss trend, and mass losses of the seven polymers are accelerated with the increase of an acidity. On the other hand, with the enhancement of a hydrophobic environment around orthoester bonds, a mass loss rate is reduced and an adjustable long-lasting degradation ability is exhibited.

Example 6

Cytotoxicity Detection

Mouse embryonic fibroblasts (3T3) and human hepatocytes (QSG) each were added to a 96-well cell culture plate with $10^4$ cells per well and cultivated overnight, then the used medium was removed, and 180 μL of a fresh medium was added; then 20 μL of each of mixtures E-1' to E-7' and E-A' to E-D' was added to each well with a concentration gradient from 1 mg/mL to 5,000 mg/mL, and the cells were further cultivated for 48 h; the used medium was removed, 180 μL of a fresh medium and 20 μL of MTT (5 mg/mL) were added, and the cells were further cultivated for 4 h; the medium was removed, 150 μL of DMSO was added, and the cells were further cultivated under shaking for 10 min; and the absorbance at 570 nm was detected, a corresponding OD value was measured by a microplate reader, and a survival rate of cells in each group was calculated based on comparison with a control group. It can be seen from the results in FIGS. 3A-3D that the seven mixtures do not cause cytotoxicity, indicating excellent biocompatibility.

Example 7

Preparation of a novel liquid sustained release drug formulation with paclitaxel as an active substance, detection of in vitro release of the novel liquid sustained release drug formulation, and evaluation of a tumor suppression effect of the novel liquid sustained release drug formulation Preparation method of an injection with paclitaxel as an active substance: under protection of nitrogen, 800 mg of a mixture E-1' and 200 mg of paclitaxel were heated and mixed at 60° C., and naturally cooled to room temperature to obtain a paclitaxel injection (E-1'-PTX) in which a weight content of paclitaxel was 20% and a weight content of E-1' was 80%.

Figure 4:
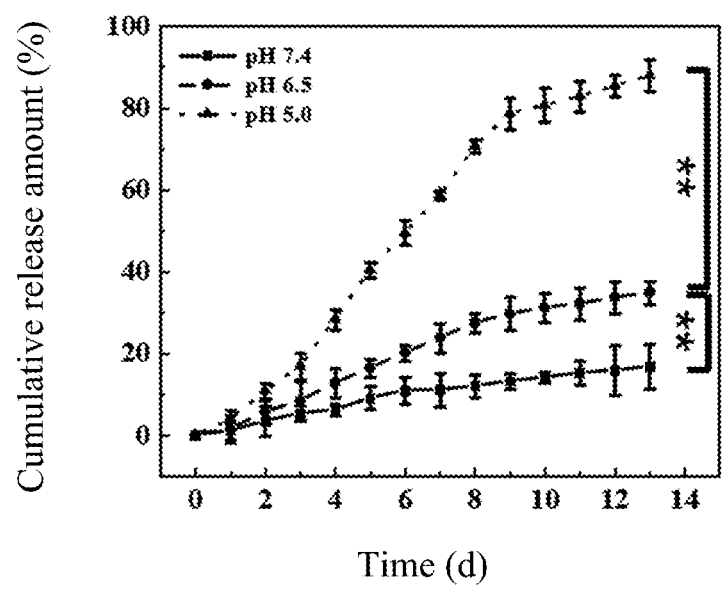
FIG. 4 shows drug release results of a paclitaxel injection in phosphate-buffered saline (PBS) at pH 7.4, 6.5, and 5.0 in Example 7 of the present disclosure.

0.5 g of the paclitaxel injection (E-1'-PTX) was accurately weighed and added to a threaded bottle with a cap, 50 mL of PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine a paclitaxel concentration, and a release amount of paclitaxel was then calculated. The above operation was repeated three times. It can be seen from the results in FIG. 4 that a drug release of the paclitaxel injection is a zero-order release and exhibits an obvious long-lasting sustained release effect, and a drug release rate is positively correlated with an acidity of the buffer.

The prepared paclitaxel injection (E-1'-PTX) was intratumorally injected into different tumor-bearing mice at a dose of 30 mg/kg based on a paclitaxel content, and then a tumor volume, a tumor mass, and a mouse body weight were recorded at different time points. It can be seen from the results in FIGS. 5A-5C that the paclitaxel injection (E-1'-PTX) can exhibit a long-lasting tumor suppression effect and significantly reduce the toxic and side effects.

Example 8

Preparation of a novel liquid sustained release drug formulation with celecoxib as an active substance, detection of in vitro release of the novel liquid sustained release drug formulation, and evaluation of an anti-inflammatory effect of the novel liquid sustained release drug formulation Preparation method of an injection with celecoxib as an active substance: under protection of nitrogen, 750 mg of E-D' and 250 mg of celecoxib were added to 20 mL of absolute ethanol, and a resulting mixture was mixed and heated at 40° C., then subjected to vacuum distillation to remove the absolute ethanol, and then cooled to room temperature to obtain a celecoxib injection (E-D'-CXB) in which a weight content of celecoxib was 25% and a weight content of E-D' was 75%.

0.5 g of the celecoxib injection (E-D'-CXB) was accurately weighed and added to a threaded bottle with a cap, PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine a celecoxib concentration, and a release amount of celecoxib was then calculated. The above operation was repeated three times. It can be seen from the results in FIG. 6 that a drug release of the celecoxib injection is a zero-order release and exhibits an obvious long-lasting sustained release effect, and a drug release rate is positively correlated with an acidity of the buffer.

Inflammation model mice were treated with the prepared celecoxib injection (E-D'-CXB) at a dose of 20 mg/kg based on a celecoxib content, where celecoxib was administered orally and the celecoxib injection (E-D'-CXB) was administered through subcutaneous injection. Expression levels of VEGF, COX-2, and prostaglandin E2 were detected on day 7 after administration. It can be seen from the results in FIGS. 7A-7C that the celecoxib injection (E-D'-CXB) can significantly reduce the expression levels of VEGF, COX-2, and prostaglandin $E_2$ in mice, indicating a significant long-lasting anti-inflammatory effect.

Example 9

Preparation of a novel liquid sustained release drug formulation with insulin as an active substance, detection of in vitro release of the novel liquid sustained release drug formulation, and evaluation of a hypoglycemic effect of the novel liquid sustained release drug formulation Preparation method of an injection with insulin as an active substance: 840 mg of E-B' and 160 mg of insulin were mixed and dissolved under reduced pressure and stirring to obtain an insulin injection (E-B'-INS) in which a weight content of insulin was 16% and a weight content of E-B' was 84%.

Figure 8:
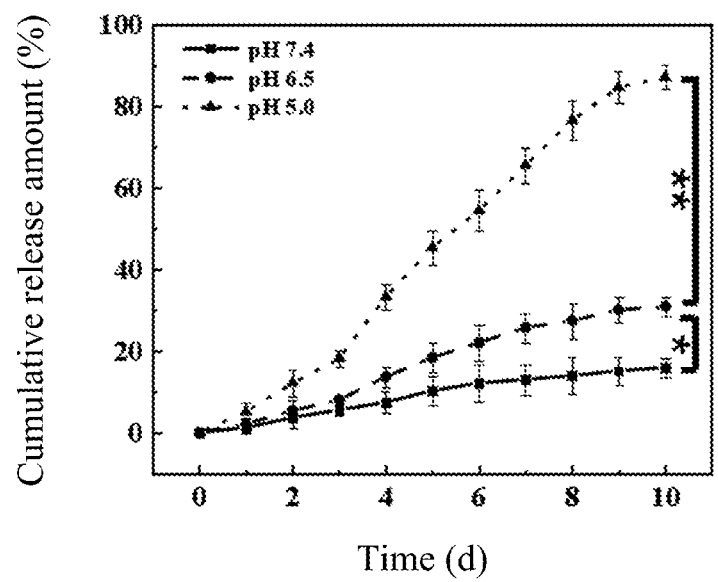
FIG. 8 shows drug release results of an insulin injection in PBS at pH 7.4, 6.5, and 5.0 in Example 9 of the present disclosure.

0.5 g of the insulin injection (E-B'-INS) was accurately weighed and added to a threaded bottle with a cap, 20 mL of PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine an insulin concentration, and a release amount of insulin was then calculated. The above operation was repeated three times. It can be seen from the results in FIG. 8 that a drug release of the insulin injection is a zero-order release and exhibits an obvious long-lasting sustained release effect, and a drug release rate is positively correlated with an acidity of the buffer.

Figure 9A:
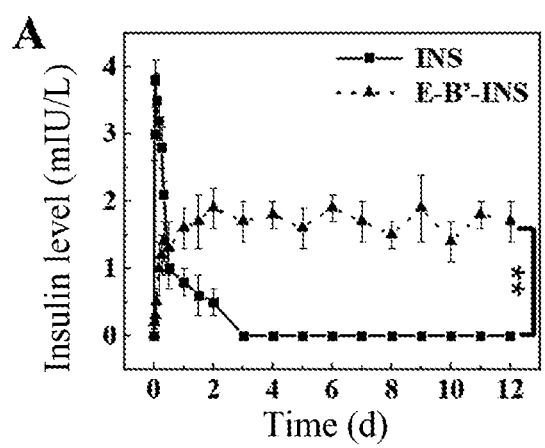
FIGS. 9A-9B show change trends of an insulin level and a blood glucose concentration in a rat diabetes model subcutaneously injected with an insulin injection in Example 9 of the present disclosure, where FIG. 9A corresponds to the insulin level and FIG. 9B corresponds to the blood glucose concentration.
Figure 9B:
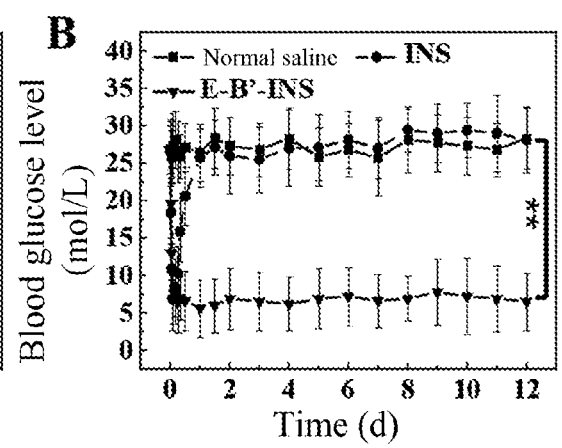

The prepared insulin injection (E-B'-INS) was injected subcutaneously into different hyperglycaemia model rats at a dose of 5 IU/kg based on an insulin content, and an insulin concentration in blood and a blood glucose level were detected. It can be seen from the results in FIGS. 9A-9B that the insulin injection (E-B'-INS) can continuously release insulin in a rat for a long time to continuously maintain a normal blood glucose level in the rat.

Example 10

Preparation of a novel liquid sustained release drug formulation with irbesartan as an active substance, detection of in vitro release of the novel liquid sustained release drug formulation, and evaluation of an antihypertensive effect of the novel liquid sustained release drug formulation Preparation method of an injection with irbesartan as an active substance: 770 mg of E-1' was mixed with 230 mg of irbesartan, and a resulting mixture was heated to 70° C. under stirring in a nitrogen atmosphere for dissolution and then cooled to room temperature to obtain an irbesartan injection (E-1'-Irbe) in which a weight content of irbesartan was 23% and a weight content of E-1' was 77%.

Figure 10:
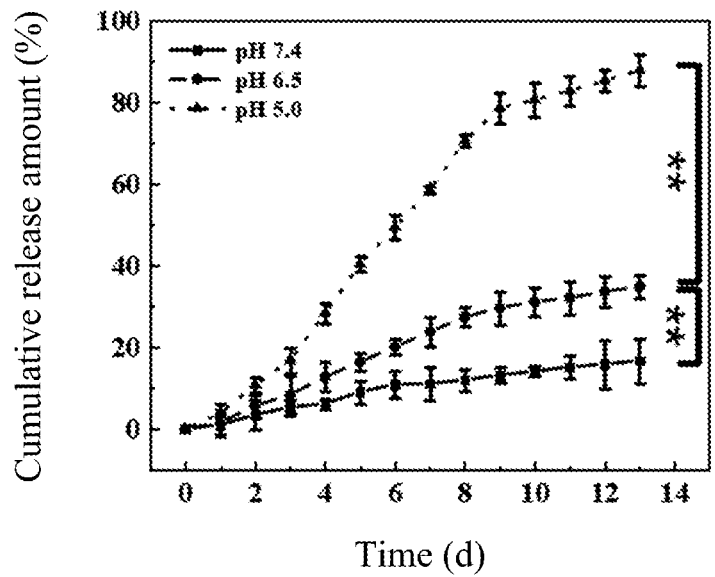
FIG. 10 shows drug release results of an irbesartan injection in PBS at pH 7.4, 6.5, and 5.0 in Example 10 of the present disclosure.

0.5 g of the irbesartan injection (E-1'-Irbe) was accurately weighed and added to a threaded bottle with a cap, 20 mL of PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine an irbesartan concentration, and a release amount of irbesartan was then calculated. The above operation was repeated three times. It can be seen from the results in FIG. 10 that a drug release of the irbesartan injection is a zero-order release and exhibits an obvious long-lasting sustained release effect, and a drug release rate is positively correlated with an acidity of the buffer.

Figure 11A:
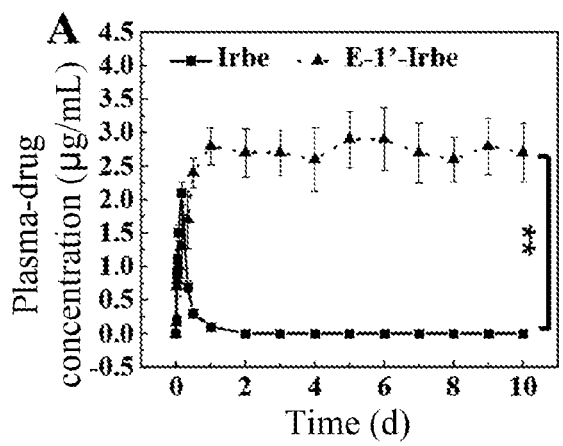
FIGS. 11A-11B show change trends of a plasma-drug concentration and a blood pressure in a rat hypertension model subcutaneously injected with an irbesartan injection in Example 10 of the present disclosure, where FIG. 11A corresponds to the plasma-drug concentration and FIG. 11B corresponds to the average blood pressure.
Figure 11B:
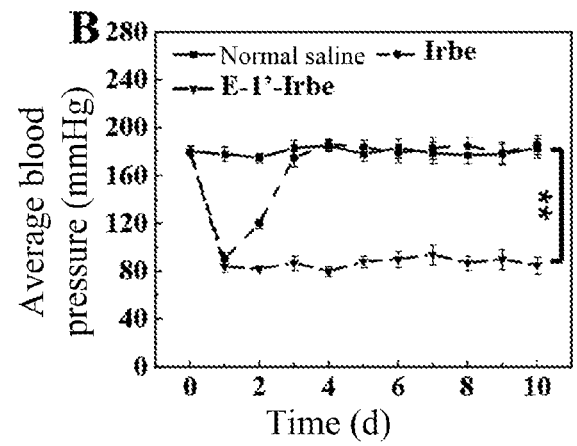

Hypertension model rats were treated with irbesartan and the prepared irbesartan injection (E-1'-Irbe) at a dose of 40 mg/kg based on an irbesartan content, where the irbesartan was administered orally and the irbesartan injection (E-1'-Irbe) was administered through subcutaneous injection. A drug concentration in blood and a blood pressure level were detected at a preset time point. It can be seen from the results in FIGS. 11A-11B that the irbesartan can reduce a blood pressure, but a concentration of the irbesartan decreases rapidly, such that a blood pressure in a rat rebounds rapidly. The irbesartan injection can continuously release irbesartan in a rat to continuously maintain a normal blood pressure level in the rat.

Example 11

Preparation of a novel liquid sustained release drug formulation with ovalbumin as an active substance and detection of an antibody-producing effect of the novel liquid sustained release drug formulation Preparation method of an injection with ovalbumin as an active substance: 950 mg of E-C' and 50 mg of ovalbumin were mechanically mixed and dissolved under reduced pressure and stirring to obtain an ovalbumin injection (E-C'-Ova) in which a weight content of ovalbumin was 5% and a weight content of E-C' was 95%.

Figure 12:
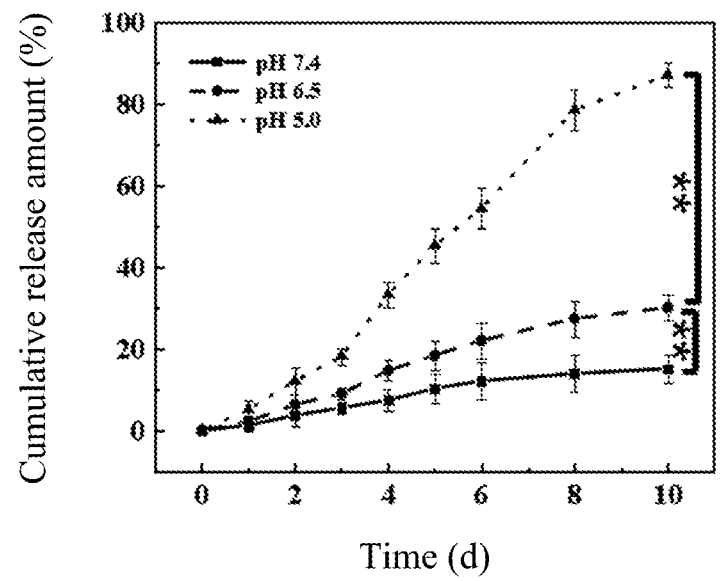
FIG. 12 shows drug release results of an ovalbumin injection in PBS at pH 7.4, 6.5, and 5.0 in Example 11 of the present disclosure.

0.5 g of the ovalbumin injection (E-C'-Ova) was accurately weighed and added to a threaded bottle with a cap, 20 mL of PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine an ovalbumin concentration, and a release amount of ovalbumin was then calculated. The above operation was repeated three times. It can be seen from the results in FIG. 12 that a drug release of the ovalbumin injection is a zero-order release and exhibits an obvious long-lasting sustained release effect, and a drug release rate is positively correlated with an acidity of the buffer.

Figure 13:
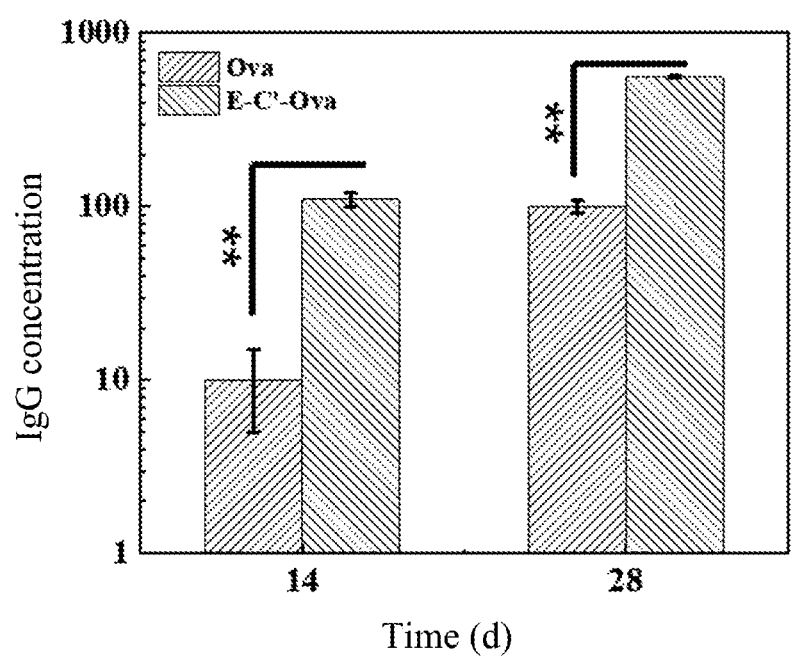
FIG. 13 shows results of an IgG antibody concentration in a mouse subcutaneously injected with an ovalbumin injection in Example 11 of the present disclosure.

Ovalbumin and the prepared ovalbumin injection (E-C'-Ova) were subcutaneously injected into different mice at a dose of 50 mg/kg based on an ovalbumin content on day 1 and day 15, and an IgG concentration was detected. It can be seen from the results in FIG. 13 that the ovalbumin can make a mouse produce a specified amount of an antibody, but a concentration of the antibody decreases rapidly; and the ovalbumin injection (E-C'-Ova) can continuously release ovalbumin in a mouse to continuously maintain a high antibody level in the mouse, thereby allowing a prominent immunization effect.

Example 12

Preparation of a novel liquid sustained release drug formulation with mepivacaine as an active substance and evaluation of an analgesic effect of the novel liquid sustained release drug formulation Preparation method of an injection with mepivacaine as an active substance: 550 mg of E-A' was mixed with 450 mg of mepivacaine, and a resulting mixture was heated to 45° C. under stirring in a nitrogen atmosphere for dissolution and then cooled to room temperature to obtain a mepivacaine injection (E-A'-Mep) in which a weight content of mepivacaine was 45% and a weight content of E-A' was 55%.

Figure 14:
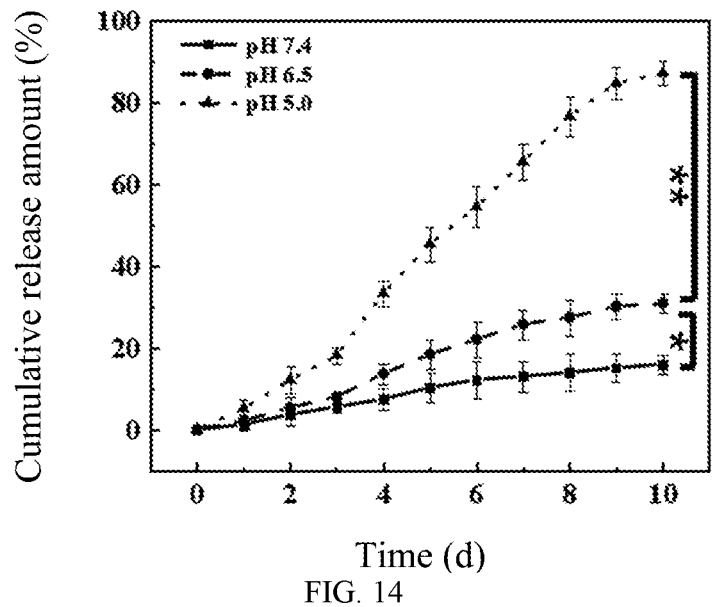
FIG. 14 shows drug release results of a mepivacaine injection in PBS at pH 7.4, 6.5, and 5.0 in Example 12 of the present disclosure.
Figure 15A:
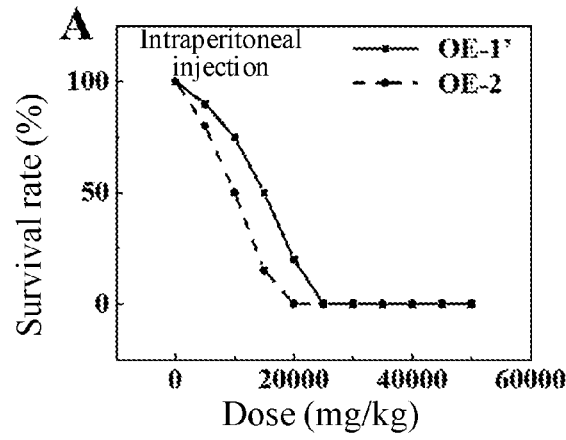
FIGS. 15A-15D show results of acute toxicity and maximum tolerated dose (MTD) of each of OE-1' and OE-2 injected into a mouse through different routes in Example 13 of the present disclosure, where
Figure 15B:
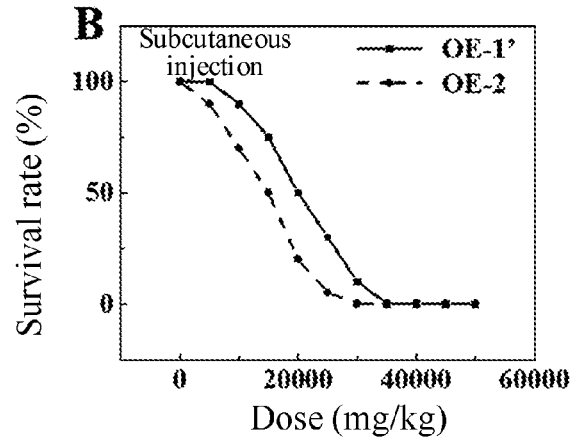
Figure 15C:
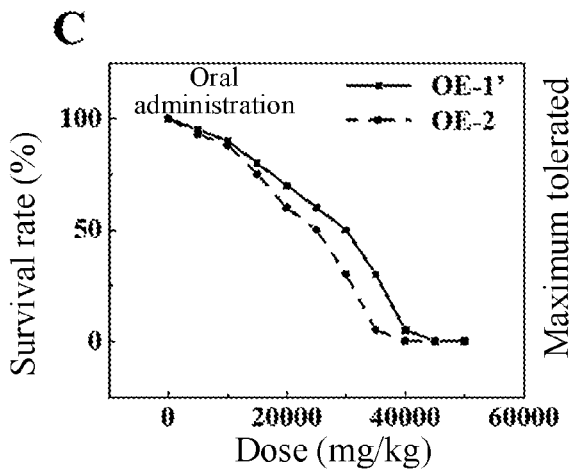
Figure 15D:
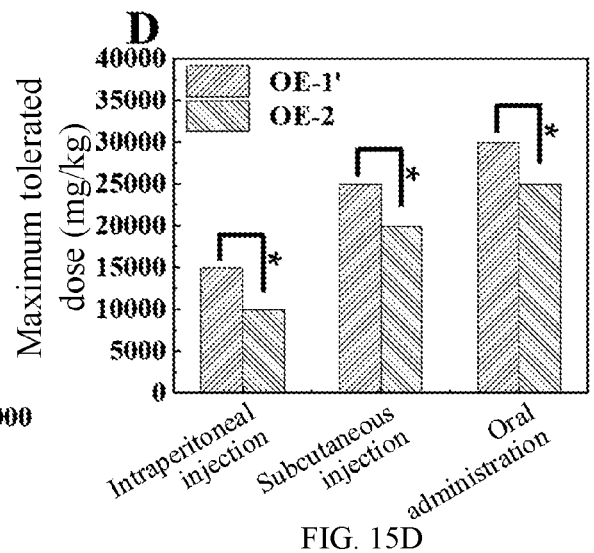

0.5 g of the mepivacaine injection (E-A'-Mep) was accurately weighed and added to a threaded bottle with a cap, 20 mL of PBS at pH 5.0, 6.5, and 7.4 was added to the threaded bottle, and the threaded bottle was allowed to stand at 37° C.; the threaded bottle was taken out at a preset time point, the PBS in the threaded bottle was collected, a same amount of a fresh buffer was added, and the threaded bottle was further allowed to stand; and then 1 mL of the original buffer was taken to determine a mepivacaine concentration, and a release amount of mepivacaine was then calculated. The above operation was repeated three times. It can be seen from the results in FIG. 14 that a drug release of the mepivacaine injection is a zero-order release and exhibits an obvious long-lasting sustained release effect, and a drug release rate is positively correlated with an acidity of the buffer.

Mepivacaine and the prepared mepivacaine injection (E-A'-Mep) each were subcutaneously injected into different pain model rats at a dose of 200 mg/kg based on a mepivacaine content. A time required for a rat to have a normal response to deep pain and electric stimulation and a time required for a rat to return from a motor weakness state to a normal state were then recorded; and when half of rats returned to a normal state, the test was stopped. Recorded results are shown in Table 1. A duration of an analgesic effect of the mepivacaine injection (E-A'-Mep) is significantly longer than a duration of an analgesic effect of the mepivacaine alone, indicating a prominent therapeutic effect.

TABLE 1

Therapeutic outcomes of the mepivacaine injection and the mepivacaine alone

| | Time required for half of rats to have a normal response (min) | | |
|---|---|---|---|
| | Deep pain | Motor weakness | Electric stimulation |
| Normal saline (NS) + mepivacaine | 60 | 60 | 60 |
| E-A'-mepivacaine | 1500 | 760 | 750 |

Example 13

With OE-2 in the patent application 202111500943.7 as a reference formulation, the OE-1' obtained in Example 1 was subjected to an acute toxicity test, and experimental steps were as follows:

OE-2 and OE-1' each were administered to different mice at a time through intragastric administration, subcutaneous injection, and intraperitoneal injection with a dose gradient from 1 mg/kg to 50,000 mg/kg; poisoning characteristics of mice within 24 h were observed, and a mortality rate was counted; and an accurate $LD_{50}$ value was calculated according to the probability unit method and the karber's method, and finally experimental groups were compared in terms of acute toxicity. It can be seen from the results in FIGS. 15A-15D that, during the treatment of the mice with OE-1' and OE-2 through different administration routes, a tolerance dose of mice for OE-1' is higher than a tolerance dose of mice for OE-2, and an $LD_{50}$ value of OE-1' is significantly higher than an $LD_{50}$ value of OE-2, indicating that the improved orthoester compound has high biosafety.

Note: The larger the $LD_{50}$ value in the experimental group, the smaller the acute toxicity.

Example 14

With OE-2 in the patent application 202111500943.7 as a reference formulation, the OE-1' obtained in Example 1 was subjected to a hemolysis test, and experimental steps were as follows:

Preparation of test samples: negative control: 2.5 mL of a red blood cell (RBC) suspension+2.5 mL of a 0.9% sodium chloride injection; positive control: 2.5 mL of an RBC suspension+2.5 mL of distilled water; and experimental group: 2.5 mL of an RBC suspension+2.2 mL of a 0.9% sodium chloride injection+0.3 mL of a formulation to be tested (3 mg/mL to 15 mg/mL).

Figure 16:
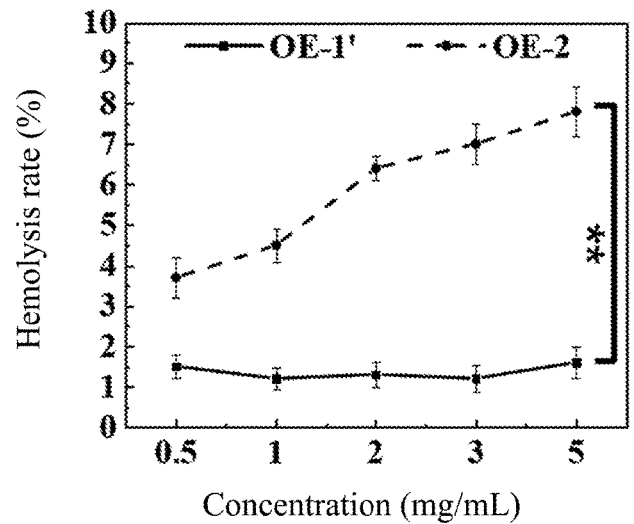
FIG. 16 shows results of hemolysis rates of OE-1' and OE-2 in Example 14 of the present disclosure.

Each sample was incubated in a 37° C. thermostatic water bath for 3 h and then centrifuged (3,000 r/min, 5 min) to obtain a supernatant, the supernatant was allowed to stand at room temperature for 30 min, and the absorbance of the sample was determined at 540 nm by a microplate reader; and the influence of plasma contents was eliminated with the absorbance of the negative control group, and then a hemolysis rate (%) of the experimental group could be calculated according to the following formula:

$$HL\% = At/Apc \times 100\%,$$

where At represents an absorbance value of a test sample and APC represents an absorbance value of the positive control. When a hemolysis rate is lower than 5%, it means that the formulation of the experimental group has no hemolytic effect at a corresponding concentration. It can be seen from the results in FIG. 16 that the OE-1' group does not lead to a hemolytic effect, but the OE-2 group leads to a slight hemolytic effect, indicating that the improved orthoester compound has excellent biosafety.

Example 15

Figure 17A:
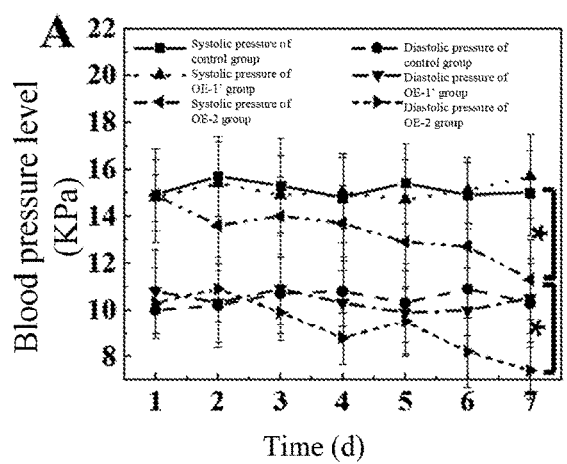
FIGS. 17A-17B show changes of a blood pressure level and a heart rate in mice subcutaneously injected with OE-1' and OE-2 in Example 15 of the present disclosure, where
Figure 17B:
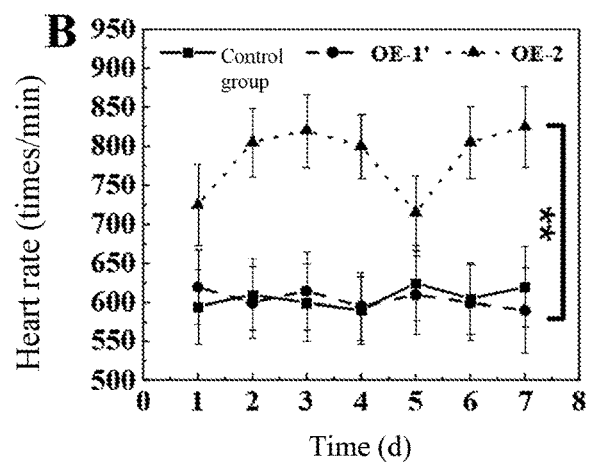

With OE-2 in the patent application 202111500943.7 as a reference formulation, the OE-1' obtained in Example 1 was subjected to cardiovascular system-associated safety evaluation, and experimental steps were as follows:

Different formulations each were subcutaneously injected into different mice at a dose of 15,000 mg/kg, and a blood pressure and a heart rate of mice in each group were measured daily by a whole-body plethysmograph (WBP) in the following week. It can be seen from the results in FIGS. 17A-17B that a cardiovascular function of mice in the OE-1' group is at a normal level and mice in the OE-2 group undergo hypotension and arrhythmia, that is, only mice treated with OE-2 undergo a cardiovascular damage, indicating the biosafety of the improved orthoester compound.

Example 16

With OE-2 in the patent application 202111500943.7 as a reference formulation, the OE-1' obtained in Example 1 was subjected to respiratory system and blood oxygen saturation tests in animals, and experimental steps were as follows:

Different formulations each were subcutaneously injected into different mice at a dose of 15,000 mg/kg, and a breathing rate and a blood oxygen saturation of mice in each group were measured daily by a small animal non-invasive pulse oximeter in the following week. It can be seen from the results in FIGS. 18A-18B that a breathing rate and a blood oxygen saturation of mice in the OE-1' group are at normal levels, and mice in the OE-2 group have an increased breathing rate and a decreased blood oxygen saturation, that is, only mice treated with OE-2 undergo a myocardial damage, indicating the biosafety of the improved orthoester compound.

Example 17

With OE-2 in the patent application 202111500943.7 as a reference formulation, the OE-1' obtained in Example 1 was subjected to an alcohol metabolite biodistribution test, and experimental steps were as follows:

Preparation of standard solutions: an appropriate amount of methanol or ethanol was accurately weighed and prepared with water into a 10.0 mg/mL standard solution as a stock solution, and the stock solution was further diluted into aqueous solutions with concentrations of 0.10 mg/mL, 0.20 mg/mL, 0.50 mg/mL, 0.80 mg/mL, 1.00 mg/mL, 2.00 mg/mL, and 3.00 mg/mL, respectively. Preparation of an internal standard solution: an appropriate amount of tert-butyl alcohol (TBA) was accurately weighed and prepared with water into a 5.0 mg/mL TBA stock solution, the TBA stock solution was diluted with water to obtain a 40.0 μg/mL TBA working solution, and the TBA working solution was refrigerated and stored in a closed manner.

Different formulations each were subcutaneously injected into different mice at a dose of 15,000 mg/kg, and then the urine, blood, heart, liver, spleen, lung, and kidney were collected from the mice at different time points. 0.10 mL of each of the standard solutions, urine, blood, and tissue extracts was taken and mixed with 0.50 mL of a 40.0 μg/mL TBA working solution, and a resulting mixture was tested by a gas chromatograph. A standard curve with a linear regression coefficient of 0.999 or higher was plotted with results of the standard solutions, and then a methanol or ethanol content in each sample was calculated. It can be seen from the results in FIGS. 19A-19B that a trace amount of ethanol is detected in each sample of the OE-1' group, and a methanol content detected in each sample of the OE-2 group is significantly high and is mostly distributed in the liver, indicating that the methanol metabolite of the orthoester can hardly be metabolized or cleared rapidly in mice like the ethanol metabolite, and may accumulate in the liver for a long time to cause serious hepatotoxicity. Therefore, the improved orthoester compound has excellent biosafety.

Example 18

With OE-2 in the patent application 202111500943.7 as a reference formulation, the OE-1' obtained in Example 1 was subjected to a chronic toxicity test in animals, and experimental steps were as follows:

Different formulations each were subcutaneously injected into different mice at a dose of 15,000 mg/kg, and the continuous behavioral observation, routine blood test, biochemical index test, and organ weight measurement were conducted for 6 months.

Figure 20:
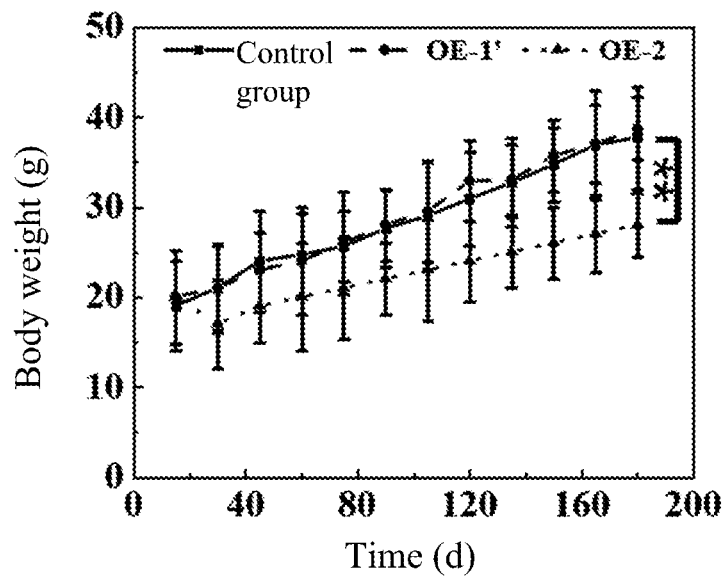
FIG. 20 shows changes of body weights of mice subcutaneously injected with 0E-1' and OE-2 in Example 18 of the present disclosure.
Figure 21:
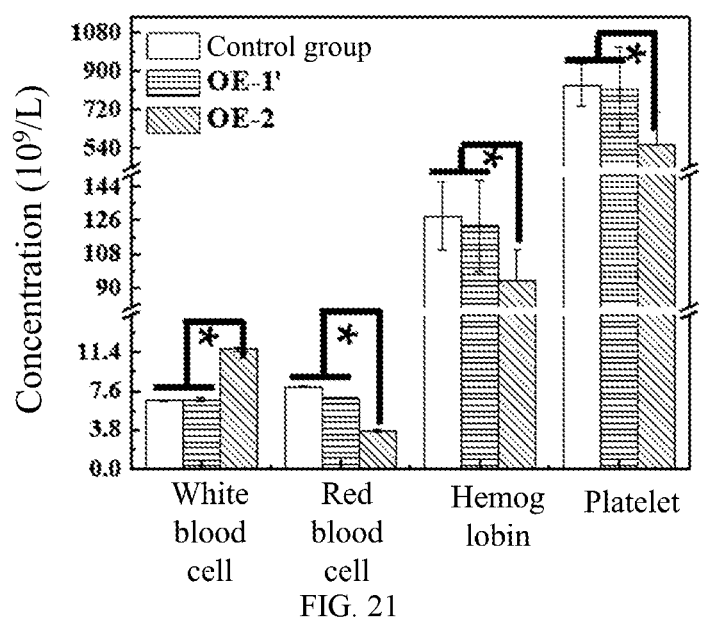
FIG. 21 shows routine blood test results of mice subcutaneously injected with OE-1' and OE-2 in Example 18 of the present disclosure.
Figure 22A:
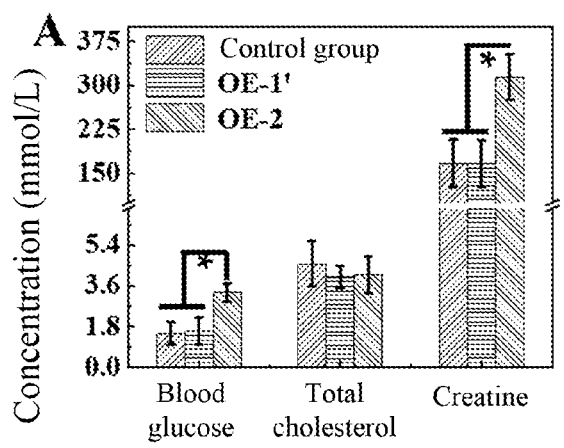
FIGS. 22A-22B show biochemical indexes of mice subcutaneously injected with OE-1' and OE-2 in Example 18 of the present disclosure.
Figure 22B:
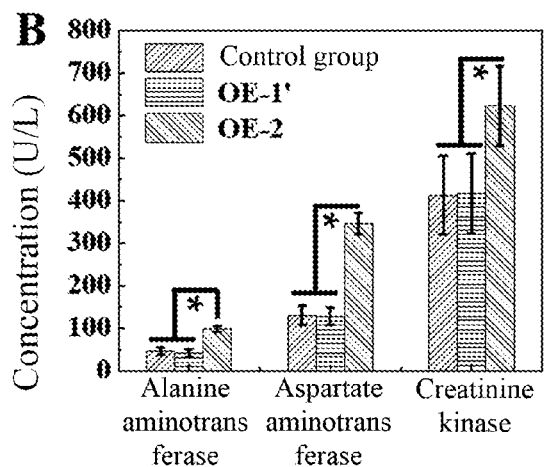
Figure 23:
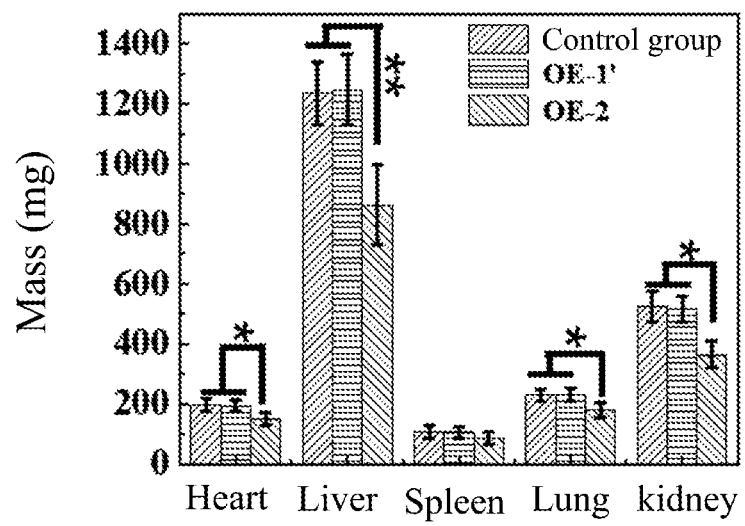
FIG. 23 shows organ weights of mice subcutaneously injected with OE-1' and OE-2 in Example 18 of the present disclosure.

It can be seen from the results in FIG. 20 that a body weight gain of mice in the OE-2 group is significantly less than a body weight gain of mice in the OE-1' group, indicating that OE-2 hinders the normal growth of mice. It can be seen from the results in FIG. 21 that, compared with the NS group and the OE-1' group, contents of white blood cells (WBCs), blood cells, hemoglobin, and platelets in mice of the OE-2 group all are at abnormal levels, indicating that OE-2 triggers the hematotoxicity in the mice. It can be seen from the results in FIGS. 22A-22B that, compared with the NS group and the OE-1' group, a blood glucose level in mice of the OE-2 group is abnormal, which is attributed to the strong irritation of OE-2; and creatine, alanine aminotransferase (ALT), aspartate aminotransferase (AST), and creatinine kinase levels in mice of the OE-2 group all are abnormal, indicating that OE-2 causes a damage to the cardiac muscle, skeletal muscle, brain tissue, and liver tissue in the mice. It can be seen from the results in FIG. 23 that organ masses of mice in the NS group and the OE-1' group are significantly higher than an organ mass of mice in the OE-2 group, indicating that OE-2 exhibits systemic toxicity for mice to some degree. The above results indicate that the improved orthoester compound has excellent biosafety.

The above examples are merely used to explain rather than limit the technical solutions of the present disclosure. Although the present disclosure is described in detail with reference to the above examples, those of ordinary skill in the art should understand that they can still modify the technical solutions described in the above examples, or make equivalent substitutions to some technical features therein; and these modifications or substitutions do not make the essence of the corresponding technical solutions depart from the spirit and scope of the technical solutions of the examples of the present disclosure.

What is claimed is:

1. An improved low-toxicity and high-efficiency orthoester mixture pharmaceutical adjuvant obtained by mixing methoxy-free orthoester compounds of class I or mixing a methoxy-free orthoester compound of class I with a biocompatible medical polymer material,
wherein the methoxy-free orthoester compound of class I has a chemical formula shown in formula I:

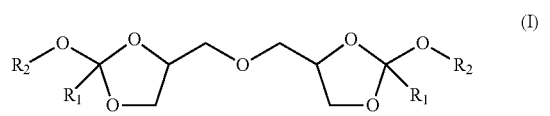

(I)

wherein $R_1$ is selected from the group consisting of hydrogen, methyl, ethyl, propyl, isopropyl, butyl, and phenyl, and $R_2$ is selected from the group consisting of ethyl, propyl, isopropyl, butyl, isobutyl, and tert-butyl.

2. The improved low-toxicity and high-efficiency orthoester mixture pharmaceutical adjuvant according to claim 1, wherein a ratio of the methoxy-free orthoester compound of class I to the biocompatible medical polymer material is 1:1,000 to 1,000:1.

3. The improved low-toxicity and high-efficiency orthoester mixture pharmaceutical adjuvant according to claim 1, wherein the biocompatible medical polymer material is selected from the group consisting of:
(i) polycaprolactone (PCL)

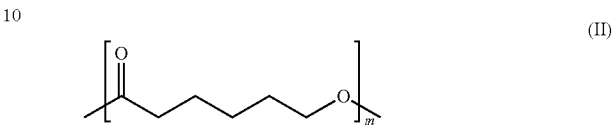

(II)

wherein m represents an integer of 2 to 100;
(ii) polycaprolactone diol (PCL-diol)

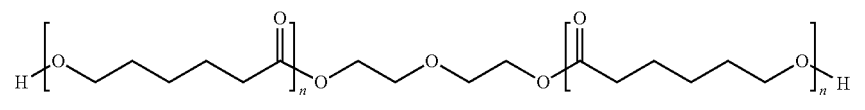

(III)

wherein n represents an integer of 1 to 50;
(iii) polylactic acid (PLA)

(IV)

wherein x represents an integer of 2 to 100; and
(iv) polyethylene glycol (PEG)

(V)

wherein y represents an integer of 2 to 150.

4. The improved low-toxicity and high-efficiency orthoester mixture pharmaceutical adjuvant according to claim 1, wherein a preparation method of the methoxy-free orthoester compound of class I comprises the following steps: under a protection of nitrogen, dissolving diglycerol, a triester, and a catalyst in a molar ratio of 1:(2.2-5.0):(0.01-0.04) in a first organic solvent, and stirring a resulting solution at room temperature to allow a reaction for 12 h to 48 h; and conducting an extraction with saturated sodium carbonate, drying a resulting extract solution with anhydrous magnesium sulfate, and conducting a vacuum distillation to remove an excess triester to obtain the methoxy-free orthoester compound of class I.

5. The improved low-toxicity and high-efficiency orthoester mixture pharmaceutical adjuvant according to claim 4, wherein the first organic solvent is selected from the group consisting of acetonitrile, dichloromethane (DCM), tetrahydrofuran (THF), and dioxane; the triester is selected from the group consisting of triethyl orthoformate, triethyl orthoacetate, triethyl orthopropionate, triethyl orthoisopropionate, triethyl orthobutyrate, triethyl orthobenzoate, tripropyl orthoformate, tripropyl orthoacetate, tripropyl orthopropionate, tripropyl orthoisopropionate, tripropyl orthobutyrate, tripropyl orthobenzoate, triisopropyl orthoformate, triisopropyl orthoacetate, triisopropyl orthopropionate, triisopropyl orthoisopropionate, triisopropyl orthobutyrate, triisopropyl orthobenzoate, tributyl orthoformate, tributyl orthoacetate, tributyl orthopropionate, tributyl orthoisopropionate, tributyl orthobutyrate, tributyl orthobenzoate, triisobutyl orthoformate, triisobutyl orthoacetate, triisobutyl orthopropionate, triisobutyl orthoisopropionate, triisobutyl orthobutyrate, triisobutyl orthobenzoate, tri-tert-butyl orthoformate, tri-tert-butyl orthoacetate, tri-tert-butyl orthopropionate, tri-tert-butyl orthoisopropionate, tri-tert-butyl orthobutyrate, and tri-tert-butyl orthobenzoate.

6. A preparation method of the improved low-toxicity and high-efficiency orthoester mixture pharmaceutical adjuvant according to claim 1, comprising the following step: mixing the methoxy-free orthoester compounds of class I or mixing the methoxy-free orthoester compound of class I with the biocompatible medical polymer material, wherein the mixing is conducted at 25° C. to 140° C. under a negative pressure or at 25° C. to 140° C. in a nitrogen atmosphere; or raw materials are first dissolved in a second organic solvent, and then the second organic solvent is removed under a reduced pressure.

7. The preparation method of the improved low-toxicity and high-efficiency orthoester mixture pharmaceutical adjuvant according to claim 6, wherein the second organic solvent is selected from the group consisting of THF, DCM, dioxane, ethanol, methanol, chloroform, acetone, dimethyl sulfoxide (DMSO), and N,N-dimethylformamide (DMF).

8. A topical sustained release drug delivery formulation comprising the improved low-toxicity and high-efficiency orthoester mixture pharmaceutical adjuvant according to claim 1 and an active substance, wherein a weight percentage of the active substance is 0.1% to 50%, and a weight percentage of the improved low-toxicity and high-efficiency orthoester mixture pharmaceutical adjuvant is 50% to 99.9%.

9. The topical sustained release drug delivery formulation according to claim 8, wherein the active substance is one or more selected from the group consisting of an antitumor drug, an anti-inflammatory drug, a hypoglycemic drug, an antihypertensive drug, an analgesic drug, and a protein vaccine.

10. The topical sustained release drug delivery formulation according to claim 9, wherein the antitumor drug is one selected from the group consisting of paclitaxel, doxorubicin, gemcitabine, 5-fluorouracil, camptothecin, hydroxycamptothecin, cisplatin, carboplatin, PD-1, gefitinib, erlotinib, sorafenib, and dasatinib.

11. The topical sustained release drug delivery formulation according to claim 9, wherein the anti-inflammatory drug is one selected from the group consisting of aspirin, sodium diclofenac, ibuprofen, flurbiprofen, ketoprofen, naproxen, indobufen, indomethacin, piroxicam, meloxicam, imrecoxib, celecoxib, dexamethasone, hydrocortisone, prednisolone, methylprednisolone, triamcinolone acetonide, fluocinolone, fludrocortisone, and beclomethasone.

12. The topical sustained release drug delivery formulation according to claim 9, wherein the antihypertensive drug is selected from the group consisting of a thiazide, a potassium-sparing diuretic, an aldosterone antagonist, a loop diuretic, a central antihypertensive drug, a ganglion-blocking drug, a noradrenergic nerve ending-blocking drug, an adrenoceptor-blocking drug, an angiotensin-converting enzyme (ACE) inhibitor, an angiotensin II receptor-blocking drug, a renin inhibitor, a dihydropyridine, and a vasodilator.

13. The topical sustained release drug delivery formulation according to claim 9, wherein the analgesic drug is selected from the group consisting of a receptor agonist, a receptor partial agonist, an opioid receptor antagonist, and an antipyretic analgesic.

14. The topical sustained release drug delivery formulation according to claim 9, wherein the protein vaccine comprises a natural protein and a chemically-inactivated toxoid.

15. The preparation method of the improved low-toxicity and high-efficiency orthoester mixture pharmaceutical adjuvant according to claim 6, wherein a ratio of the methoxy-free orthoester compound of class I to the biocompatible medical polymer material is 1:1,000 to 1,000:1.

16. The preparation method of the improved low-toxicity and high-efficiency orthoester mixture pharmaceutical adjuvant according to claim 6, wherein the biocompatible medical polymer material is selected from the group consisting of:

(i) PCL

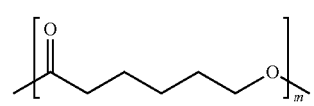

(II)

wherein m represents an integer of 2 to 100;

(ii) PCL-diol

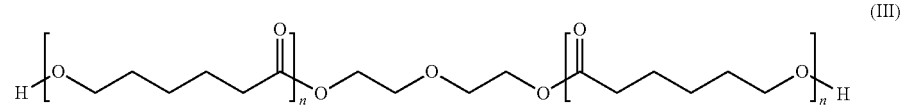

(III)

wherein n represents an integer of 1 to 50;

(iii) PLA

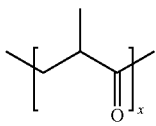
(IV)

wherein x represents an integer of 2 to 100; and (iv) PEG

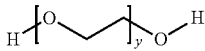
(V)

wherein y represents an integer of 2 to 150.

17. The preparation method of the improved low-toxicity and high-efficiency orthoester mixture pharmaceutical adjuvant according to claim 6, wherein a preparation method of the methoxy-free orthoester compound of class I comprises the following steps: under a protection of nitrogen, dissolving diglycerol, a triester, and a catalyst in a molar ratio of 1:(2.2-5.0):(0.01-0.04) in a first organic solvent, and stirring a resulting solution at room temperature to allow a reaction for 12 h to 48 h; and conducting an extraction with saturated sodium carbonate, drying a resulting extract solution with anhydrous magnesium sulfate, and conducting a vacuum distillation to remove an excess triester to obtain the methoxy-free orthoester compound of class I.

18. The preparation method of the improved low-toxicity and high-efficiency orthoester mixture pharmaceutical adjuvant according to claim 17, wherein the first organic solvent is selected from the group consisting of acetonitrile, DCM, THF, and dioxane; the triester is selected from the group consisting of triethyl orthoformate, triethyl orthoacetate, triethyl orthopropionate, triethyl orthoisopropionate, triethyl orthobutyrate, triethyl orthobenzoate, tripropyl orthoformate, tripropyl orthoacetate, tripropyl orthopropionate, tripropyl orthoisopropionate, tripropyl orthobutyrate, tripropyl orthobenzoate, triisopropyl orthoformate, triisopropyl orthoacetate, triisopropyl orthopropionate, triisopropyl orthoisopropionate, triisopropyl orthobutyrate, triisopropyl orthobenzoate, tributyl orthoformate, tributyl orthoacetate, tributyl orthopropionate, tributyl orthoisopropionate, tributyl orthobutyrate, tributyl orthobenzoate, triisobutyl orthoformate, triisobutyl orthoacetate, triisobutyl orthopropionate, triisobutyl orthoisopropionate, triisobutyl orthobutyrate, triisobutyl orthobenzoate, tri-tert-butyl orthoformate, tri-tert-butyl orthoacetate, tri-tert-butyl orthopropionate, tri-tert-butyl orthoisopropionate, tri-tert-butyl orthobutyrate, and tri-tert-butyl orthobenzoate.

19. The topical sustained release drug delivery formulation according to claim 8, wherein in the improved low-toxicity and high-efficiency orthoester mixture pharmaceutical adjuvant, a ratio of the methoxy-free orthoester compound of class I to the biocompatible medical polymer material is 1:1,000 to 1,000:1.

20. The topical sustained release drug delivery formulation according to claim 8, wherein in the improved low-toxicity and high-efficiency orthoester mixture pharmaceutical adjuvant, the biocompatible medical polymer material is selected from the group consisting of:

(i) PCL

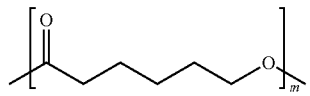
(II)

wherein m represents an integer of 2 to 100;

(ii) PCL-diol

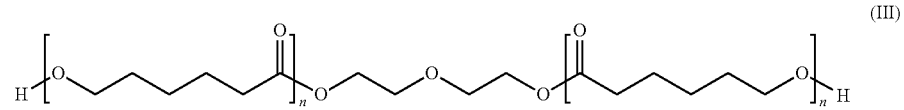
(III)

wherein n represents an integer of 1 to 50;
(iii) PLA
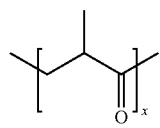
(IV)
wherein x represents an integer of 2 to 100; and
(iv) PEG
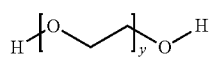
(V)
wherein y represents an integer of 2 to 150.
* * * * *